(12) United States Patent
Hiltbrand

(10) Patent No.: US 8,695,444 B2
(45) Date of Patent: Apr. 15, 2014

(54) TOOL FOR HANDLING A SAMPLE

(75) Inventor: Roland Hiltbrand, Zofingen (CH)

(73) Assignee: CTC Analytics AG, Zwingen (CH)

( * ) Notice: Subject to any disclaimer, the term of this patent is extended or adjusted under 35 U.S.C. 154(b) by 244 days.

(21) Appl. No.: 12/814,169

(22) Filed: Jun. 11, 2010

(65) Prior Publication Data
US 2010/0313688 A1 Dec. 16, 2010

(30) Foreign Application Priority Data
Jun. 12, 2009 (EP) .................................. 09 405 100

(51) Int. Cl.
*G01N 1/14* (2006.01)

(52) U.S. Cl.
USPC ...................................... 73/864.14

(58) Field of Classification Search
USPC ............................. 73/864.14, 864
See application file for complete search history.

(56) References Cited

U.S. PATENT DOCUMENTS

| | | | |
|---|---|---|---|
| 4,621,534 A | 11/1986 | Munari et al. | |
| 5,756,905 A | 5/1998 | Ueda | |
| 5,906,795 A * | 5/1999 | Nakashima et al. | 422/509 |
| 8,420,027 B2 | 4/2013 | Mahler et al. | |
| 2003/0233893 A1 | 12/2003 | Bremer et al. | |
| 2004/0044439 A1 * | 3/2004 | Gueller et al. | 700/240 |
| 2004/0047765 A1 | 3/2004 | Gordon et al. | |
| 2005/0013744 A1 * | 1/2005 | Nagai et al. | 422/100 |
| 2007/0034662 A1 * | 2/2007 | Opper et al. | 227/51 |
| 2007/0137320 A1 | 6/2007 | Bremer et al. | |
| 2007/0140904 A1 | 6/2007 | Bremer et al. | |
| 2007/0167952 A1 * | 7/2007 | Burgi et al. | 606/99 |
| 2008/0240898 A1 | 10/2008 | Manz et al. | |
| 2009/0016931 A1 * | 1/2009 | Seino et al. | 422/63 |

FOREIGN PATENT DOCUMENTS

| | | |
|---|---|---|
| CN | 201 170 097 Y | 12/2008 |
| DE | 102 19 790 C1 | 10/2003 |
| DE | 10 2005 049920 A1 | 4/2007 |
| DE | 20 2007 014286 U1 | 4/2009 |
| EP | 1 798 551 A1 | 6/2007 |
| WO | 2007/032039 A2 | 3/2007 |

* cited by examiner

*Primary Examiner* — Herzon E Williams
*Assistant Examiner* — Nashmiya Fayyaz
(74) *Attorney, Agent, or Firm* — Birch, Stewart, Kolasch & Birch, LLP

(57) ABSTRACT

In the case of a tool (140) for handling a sample, which comprises a fastening device (141) for detachably fastening the tool to a tool holder of a sample handling apparatus, and comprises a sample manipulation device, for example realized as a syringe (150), fastened to the fastening device (141), this tool comprises a holding device, for example in the form of a needle guide (160), which, on the one hand, is fastened to the fastening device (141) so as to be movable in a coupling direction (165) and, on the other hand, can be coupled to and decoupled from the tool holder in the coupling direction (165).

15 Claims, 4 Drawing Sheets

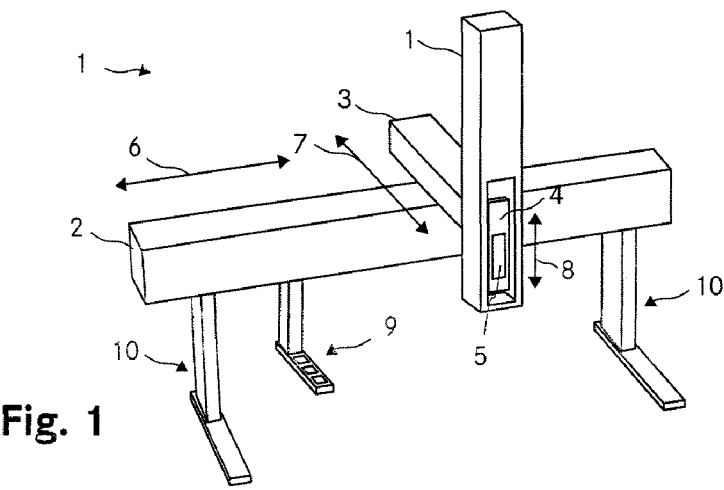
Fig. 1
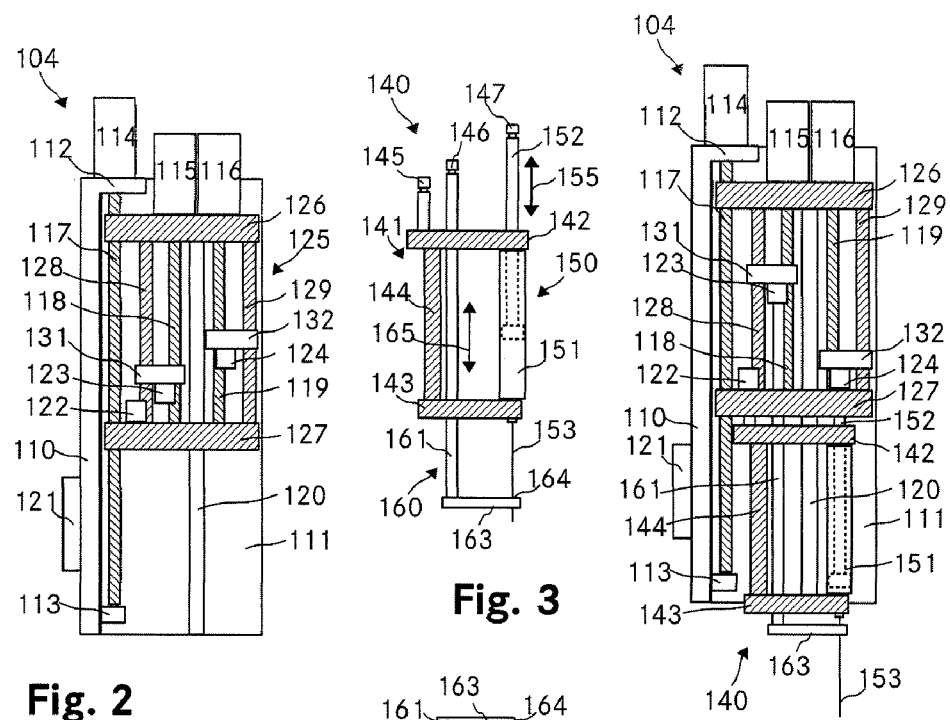
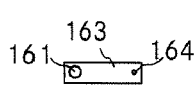
Fig. 2
Fig. 3
Fig. 4   Fig. 5

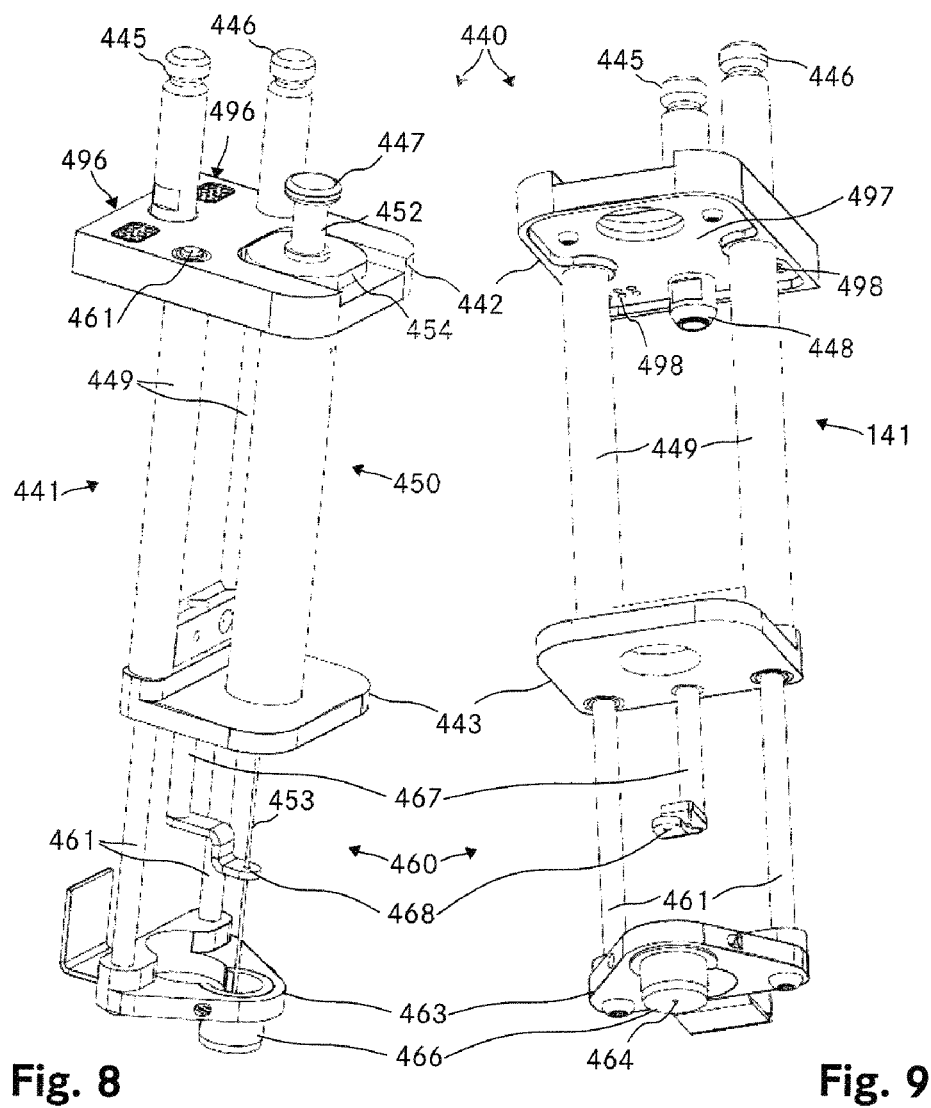
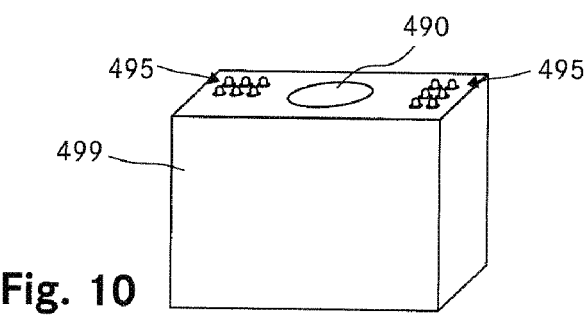
Fig. 8    Fig. 9
Fig. 10

TOOL FOR HANDLING A SAMPLE

TECHNICAL DOMAIN

The invention relates to a tool for handling a sample, comprising a fastening device for detachably fastening the tool to a tool holder of a sample handling apparatus, and comprising a sample manipulation device fastened to the fastening device. Further, the invention relates to a corresponding tool holder, a sample handling apparatus having such a tool holder, and to an arrangement having such a sample handling apparatus and at least one corresponding tool. In addition, the invention relates to a method for coupling and decoupling such a tool to and from, respectively, such a tool holder.

PRIOR ART

In the analysis of material samples, for example in gas or liquid chromatography, the demands are constantly becoming greater. On the one hand, for example, the sample quantities are becoming ever smaller while, at the same time, the sensitivity is to be increased. In addition, the number of analyses to be conducted is to be increased constantly.

For the largely automatic analysis of samples, so-called autosamplers are known, which undertake the handling of a sample before it is supplied, in an appropriate form and dosage, to the analysis device. The handling of the sample is effected by means of various tools, for example various types of syringes for receiving the sample from a storage container and delivering the sample into an analysis device. These tools are fastened to such a device, but typically have to be exchanged manually.

Known from DE 102 19 790 C1 by Gerstel is a further such device, but one which enables such tools to be changed automatically. The tool comprises a syringe (16) fastened to a holder (17), the syringe having a needle (29) and having a head (49) for moving the syringe piston. This holder (17) is hung in a receiver (6). By means of a receiver arm (4) movably fastened to the device, the holder (17), together with the syringe (16), is gripped magnetically (magnets 21 and sheet-metal strip 19), in that the receiver arm (4) is moved horizontally onto the receiver (6), the needle guide receivers (30, 32), which are slotted at the front, being moved over the needle (29) and the actuator (11) being moved over the head (49). The tool is then raised vertically in the receiver (6), such that the holder (17) is released from the horizontal locking device (42) and, at the same time, the needle guide receivers (30, 32) receive the needle guides (36). Finally, the tool is moved out horizontally. The process is reversed in order to store the tool. The receiver arm (4) is positioned horizontally over the receiver (6) and then lowered vertically, such that the holder (17) is locked horizontally in the locking device (42) and, at the same time, the needle guide receivers (30, 32) release the needle guides (36). The tool is then moved away again horizontally, being simply pulled away from the receiver arm (4), contrary to the holding force of the magnets (21).

Although this device does enable tools to be changed automatically, it nevertheless has the disadvantage that the coupling and decoupling of the tool is complicated, since this requires several sequential movements in various directions, it being necessary for the direction of movement of the tool holder to be changed several times between horizontal and vertical. In addition, the device cannot be applied flexibly, since a particular device (such as, for example, that according to FIG. 5) is also suitable only for a particular type of tools (here: syringes). This means that the receiver arm has to be realized in a particular manner for each type of tool, as is evident, for example, from the various embodiments according to FIGS. 5 and 9. In addition, owing to the filigree structure of the separate holders, or guides, for the head and for the needle of the syringe, the tool is comparatively susceptible to defects. Even the magnetic forces acting when the tool is being taken up or put down, or even relatively small inaccuracies in moving the receiver arm for taking up or putting down the tool can result in damage to the latter.

PRESENTATION OF THE INVENTION

The object of the invention is to create a tool, belonging to the technical domain mentioned at the outset, that enables a multiplicity of various tools of a sample handling apparatus to be changed automatically in a simple manner. In addition, it is intended to create a corresponding sample handling apparatus having an associated tool holder, to create a complete sample handling arrangement, and to create corresponding methods for coupling and decoupling a tool to and from, respectively, the tool holder.

The achievement of the object is defined by the features of Claim 1. The tool for handling a sample comprises a fastening device for detachably fastening the tool to a tool holder of a sample handling apparatus, and comprises a sample manipulation device fastened to the fastening device. According to the invention, the tool further comprises a holding device. This holding device, on the one hand, is movably fastened to the fastening device and, on the other hand, can be coupled to and, obviously, also decoupled from the tool holder. The holding device in this case can be coupled to and decoupled from the tool holder in the same direction in which it can be moved. In the following, this direction is referred to as the coupling direction.

In other words: the holding device, which corresponds approximately to the bars (34 and 31) present in the case of Gerstel, is realized as part of the tool and not, as in the case of Gerstel, as part of the receiver arm, i.e. as part of the tool receiver of the sample handling apparatus. In the case of the invention, consequently, the holding device is changed together with the tool, whereas, in the case of the prior art, the bars (34 and 31) remain on the receiver arm (4) when the tool is changed.

Frequently, the sample handling device is realized in such a way that it comprises a slide guide, along which a slide can be moved horizontally. The slide can only be moved, for example, horizontally along the slide guide, i.e. in one direction. Typically, however, the slide can also be moved horizontally in a direction perpendicular to the slide guide, and in this case it is referred to as a transverse slide. Further, fastened to one end of the slide, so as to be movable perpendicularly, is a tool holder that is realized as part of the slide or that is fastened to the latter. Through moving the slide horizontally on the slide guide, and moving the tool holder vertically on the slide, the tool makes it possible to move to virtually any point within a particular range.

As explained further below, the holding device can undertake a very great variety of tasks and functions. Since the holding device is now realized as part of the tool and is changed together with the latter, the holding device can be matched specifically and precisely to the respective function/s of the tool. In addition to the interface for fastening the fastening device to the tool holder, there is a further interface, for fastening the holding device to the tool holder. Consequently, any tool having a fastening device comprising these two interfaces can be coupled to a corresponding tool holder. Clearly, a tool comprising only one of these two interfaces can also be coupled to such a tool holder. Depending on the type of sample handling required, the coupling of the tool, by means of its fastening device, to the tool holder suffices, for example, without the coupling of a holding device.

Since the coupling of the holding device to the tool holder is effected in the same direction in which the holding device can be fastened to the tool holder, a significantly more simple design of the tool is achieved overall, since it is necessary for the holding device to be moved only in one direction. This results in an extremely simple operation for coupling the holding device to the tool holder, with movements in exclusively one direction of movement, namely, this coupling direction.

For clarity, it is also to be mentioned here that, in the case of an element that is movable in a particular direction, not only a movement in precisely this one spatial direction, but also in the respective opposite direction, is meant within the scope of the present description. Thus, for example, if the holding device is movable in the coupling direction on the fastening device, this means that it is movable in the coupling direction and in the corresponding opposite direction, i.e. both forwards and backwards in the coupling direction.

Since the holding device is already integrated into the tool and does not need to be coupled to the latter in a complicated manner, as in the case of Gerstel, the entire structure can additionally be realized in a simple and robust manner, which again significantly reduces the susceptibility to defects. A further factor in this is that, for example in the case of a tool comprising a syringe for handling the sample, the needle does not have to be threaded into and out of a needle guide in a complicated manner, as in the case of the prior art, but, rather, when the tool is being taken up or put down, the needle of a syringe remains in the holding device, which can also be used for guiding the needle.

The holding device can fulfill several functions. It serves, for example, to guide an element of the sample manipulation device when the holding device is moved in the coupling direction relative to the fastening device.

It can also serve to hold a sample container if the latter is to be transported by means of the tool. It can also serve as a hold-down device in order to hold the corresponding container in position when a sample is being taken up or put down, for example to hold (or hold back) the sample container when the septum of a glass phial is being pierced by the needle of a syringe, or the needle is being withdrawn from the septum.

The holding device can also serve as a transport device, for example for transporting sample containers. For example, there are sample phials having magnetic elements, such that these phials can be gripped and transported by means of corresponding magnets on the holding device.

A device for opening containers for samples or accessories can also be provided on the holding device; for example, a magnet for opening drawers of a drawer stack.

Clearly, the holding device can be realized in such a way that it can fulfill only individual functions or, also, a plurality of these functions simultaneously.

Many of these tools used for handling a sample comprise an element, in the form of a hollow needle, by means of which, for example, a sample is removed from a container or put into a container. In the case of syringes, which are very frequently used in the case of such tools, the needle, or cannula, constitutes this element in the form of a hollow needle. Frequently, such needles are very fine, for example to enable high-precision dosing of the sample. The finer such a needle is, however, the more susceptible to defects it becomes. It can very easily become bent or broken during the handling of the sample. Thus, even the piercing of a septum may be enough to damage the needle. The holding device therefore preferably comprises a guide element, which serves to guide such an element, in the form of a hollow needle, of the sample manipulation device. Since the holding device, and consequently also the guide element, is fastened to the fastening device so as to be movable in the coupling direction, this element in the form of a hollow needle is preferably likewise aligned with its longitudinal axis in the coupling direction, and the guide element has an opening in which the element in the form of a hollow needle can be moved in the coupling direction. The element in the form of a hollow needle is threaded into this opening, the holding device typically being positioned in such a way, when the element in the form of a hollow needle is being moved, that the guide element is located in the end region of the element in the form of a hollow needle.

Depending on the application, it may suffice if this opening is not complete all the way round, and the element in the form of a hollow needle consequently can move other than exclusively in the coupling direction. Advantageously, however, the opening is complete all the way round, such that the element in the form of a hollow needle can move exclusively in the coupling direction, but any movement in another direction is blocked. This means that the delimiting line of the opening is complete, preferably corresponding substantially to a circumferential line of a cross section of the element in the form of a hollow needle. In the case of a cannula of a syringe, this circumferential line is typically circular.

In addition to this guide element, the tool can comprise an antikink device, which serves to prevent kinking of the element in the form of a hollow needle of the sample manipulation device; for example, when this element is moved in the coupling direction, for instance pierced into a septum. Such an antikink device is appropriate, in particular, in the case of long needles of a syringe, in order to prevent the needle from bending, or even kinking or breaking, in the case of a load in the coupling direction (or other direction). Such an antikink device can be fastened, for example, to the holding device, such that it can be moved with the latter relative to the sample manipulation device, but it can also be fastened to the sample manipulation device itself. Preferably, however, it is fastened to the fastening device, also being able to be detachably fastened thereto.

As already mentioned, the fastening device can be detachably fastened to a tool holder of a sample handling apparatus. It is possible, in principle, for the fastening device to be fastened to the sample handling apparatus in any manner, for example magnetically, by means of screwed or clamp connections, through establishment of a non-positive connection or through any other connection techniques, the fastening itself being able to be effected, for instance, through one or more movements in particular directions or, also, through one or more rotary movements or combinations of such movements.

In the case of a preferred embodiment of the invention, however, the fastening device can be coupled to and decoupled from the tool holder in the coupling direction. Thus, both the coupling of the tool to the tool holder and the decoupling of the tool from the tool holder, the relative movement of the holding device and of the fastening device, and the coupling of the holding device to the tool holder and the decoupling of the holding device from the tool holder are effected in one and the same coupling direction.

This coupling and decoupling is preferably effected through connecting and undoing, respectively, a positive-fit connecting device, the fastening device comprising a first connecting element and the tool holder comprising a second connecting element of this first, positive-fit connecting device. In order to achieve a high accuracy in the dosing of the sample, this first connecting device is additionally realized, advantageously, without play.

This first connecting device is realized, for example, as a plug-in coupling without play, the fastening device comprising a male coupling element of the plug-in coupling and the tool holder comprising a female coupling element of the plug-in coupling.

Since both the fastening device and the holding device can be fastened to the tool holder in the same direction, the tool can be coupled to the tool holder in a very simple manner. Since, moreover, this fastening direction, referred to as the coupling direction, also coincides with that direction in which the holding device is movable on the fastening device, the overall result is an extremely simple coupling operation with movements in exclusively one direction of movement, namely, this coupling direction. Since there is no need for movements of the tool holder or of the tool in a direction perpendicular to this coupling direction, only a small amount of space is also occupied perpendicularly to the coupling direction, such that, overall, less space is also required for storing a plurality of tools. For the same reason, the tools can also be positioned close to or directly next to other objects, which allows a more optimal use of the space available within the range of the tool holder.

The coupling direction is preferably vertical, or substantially vertical. A different alignment of this coupling direction is not usual, although not precluded from a technical aspect.

Although the sample manipulation device can be fixedly fastened to the fastening device, this device likewise is preferably detachably fastened to the fastening device, such that it can easily be replaced if necessary. Thus, for example, a syringe of a particular type can be replaced by a new syringe of the same type or by a syringe of a different type. This can be performed both, manually, by an operator, and automatically, by a corresponding change device.

As already mentioned, the holding device can also be detachably fastened to the tool holder of a sample handling apparatus. Here, likewise, as in the case of the fastening of the fastening device, it is true that the holding device can, in principle, be fastened to the tool holder on the sample handling apparatus in any manner, for instance through one or more movements in particular directions or, also, through one or more rotary movements or combinations of such movements.

In the case of a preferred embodiment of the invention, however, the holding device also can be coupled to and decoupled from the tool holder through connecting and undoing, respectively, a second positive-fit connecting device. The holding device again comprises a first connecting element and the tool holder comprises a second connecting element of this second, positive-fit connecting device. Since precise positioning of the holding device is not necessary for high accuracy in the dosing of the sample, the second connecting device can have play.

This second connecting device, likewise, is realized, for example, as a plug-in coupling, the holding device comprising a male coupling element of this plug-in coupling and the tool holder comprising a female coupling element of this plug-in coupling.

In a further preferred embodiment of the invention, such a tool comprises a movable element, in order to increase further the functional variety of the tools that can be used. Although such a movable element is not necessary and could also be omitted, it nevertheless provides for many additional functions of the tools that can be used.

The movable element could be constituted, for example, by a movable element of the sample manipulation device, for instance by the piston of a syringe. In the case of other tools, it can be realized, for example, to grip a container, actuate a pipetting aid of a pipette, actuate an opening or closing mechanism, or actuate any other movable element.

This movable element can be movable in any manner, but is preferably movable in relation to the sample manipulation device in the coupling direction. Moreover, advantageously, it can also be coupled to and decoupled from the tool holder in the coupling direction, such that this movable element is not only movable independently of the sample manipulation device in the coupling direction but, in addition, can also be coupled to and decoupled from the tool holder in the same direction. Consequently, the entire operation of coupling a tool to the tool holder and decoupling it from the tool holder continues to be effected in precisely one direction, and can therefore be performed extremely easily and also rapidly.

In principle, the movable element also can be fastened to the tool holder in any manner, but again this is preferably effected through connecting or undoing a third positive-fit connecting device. In this case, the movable element again comprises a first connecting element and the tool holder comprises a second connecting element of this third, positive-fit connecting device. In the case of this connecting device, likewise, the accuracy in the dosing of the sample can be increased through a design without play, for which reason a coupling without play is preferred.

The third connecting device also is realized, for example, as a plug-in coupling, the movable element comprising a male coupling element of this plug-in coupling and the tool holder comprising a female coupling element of this plug-in coupling.

There are many various tools for the handling of samples. They range from syringes to grippers and agitators, to any other manipulators. In addition, such tools can also undertake further functions such as, for example, heating or cooling the sample, or mixing the sample with other substances.

A tool that is used very frequently, and without which the handling of samples can scarcely be imagined, for example for take-up and dosed delivery of the sample in the case of liquid chromatography, is the syringe; specifically, syringes in a great variety of designs, for example of differing volumes, needle lengths, needle diameters, heatable, non-heatable, etc. Preferably, therefore, the sample manipulation device is realized as a syringe. The latter typically comprises a cylindrical hollow body and a piston that is movable in the hollow body, as well as a cannula, which is fastened to the syringe and which is usually realized as a hollow needle.

The hollow body is (detachably) fastened to the fastening device, the syringe piston in this case constituting the movable element and the cannula constituting the element in the form of a hollow needle.

In the case of a further preferred embodiment variant of the invention, the tool comprises a communication interface. The latter serves to establish a communication connection between the tool and the sample handling apparatus, such that, for example, the tool can transmit tool-specific information to the sample handling apparatus or the sample handling apparatus can transmit information such as, for instance, signals or commands for control to the tool. This communication interface could be realized, for example, as a wireless radio interface, or electrical signals could be transmitted through an electromagnetic, e.g. capacitive or inductive coupling between the tool and the sample handling apparatus. By means of an electromagnetic coupling, for example, electrical energy could also be transmitted from the sample handling apparatus to the tool, the latter requiring this energy for the operation of the tool, the quantity of energy that can be transmitted thus being rather small. Clearly, the tool could also be provided with a separate energy source, either its own or external, or connected to such an energy source.

In the case of a particularly preferred exemplary embodiment of such a tool having a communication interface, the tool comprises at least one electrical contact for the purpose of establishing at least one electrically conductive connection between the tool and the sample handling apparatus. Although, in principle, one electrical connection is sufficient for the transmission of data, typically there are two or more electrical contacts, such that two or more electrically conductive connections can be established between the tool and the sample handling apparatus. In this way, for example, more data can be transmitted within a shorter time or, alternatively, substantially more complex communication and control processes can be established.

If the communication interface comprises two or more electrically conductive connections, however, these can be used, not only for data transmission but also, advantageously, for transmitting energy, and specifically, in principle, even in both directions. Typically, however, electrical energy is transmitted only from the sample handling apparatus to the tool, such that the tool does not require a separate electric power supply. In the case of the tool, this electrical energy could either be used directly, for operation, or it could also be stored in an energy storage device such as, for instance, a battery or an accumulator, or also, alternatively, in a capacitive or inductive energy storage device, in which case the tool can then be operated with the energy stored in this energy storage device.

On the other hand, it is advantageous if data can be transmitted via these connections, both from the tool to the tool holder and from the tool holder to the tool. Thus, for example, the tool can transmit information relating to its state, its equipment, etc. to the sample handling apparatus, and the sample handling apparatus can transmit control signals to the tool.

In this case, data and energy could be transmitted, simultaneously or with a time offset, via the same electrical connections, but separate electrical connections are preferably provided for the transmission of data and the transmission of energy.

The electrical contact or contacts can be realized in any form, for example as plug-in or clip contacts. In order that the electrical connections can be established and disconnected automatically and as easily as possible upon the tool being coupled to and decoupled from the tool holder, respectively, the contacts preferably comprise a contact surface on one side and corresponding, for example spring-mounted, contact pins on the other side. The tool comprises, for example, a certain number of appropriately arranged contact surfaces, and the tool holder comprises a corresponding number and correspondingly arranged, spring-mounted contact pins. Clearly, the contact surfaces and contact pins can also be distributed differently. Upon the tool being coupled to the tool holder, a corresponding number of electrically conductive connections is thereby established between the tool and the sample handling apparatus. Upon decoupling of the tool, these connections are automatically disconnected.

Although these electrically conductive connections, i.e. for example the contacting between the contact surfaces and the contact pins, can be effected in any directions, these connections are also preferably established through a relative movement of the tool and of the tool holder in the coupling direction.

For the correct operation of the sample handling apparatus, the latter must know which tool is coupled to its tool holder. The sample handling apparatus could be provided with this information, for example, through programming or through a simple data input to a data processing device connected thereto.

In the case of a preferred exemplary embodiment, however, the tool comprises a memory, in particular a data memory, for example in the form of an electrical or electronic memory for the storage of data. These data can comprise, for example, tool-specific data or information such as, for instance, production date, type, manufacturer, identification code, numbers, service life, etc. This memory is then connected to the communication interface, or to the electrically conductive connection or connections, in such a way that the data stored in the memory can be transmitted to the sample handling apparatus via the communication interface, or the electrically conductive connection/s. In this way, it is also possible to verify, for example, whether a particular tool has been properly connected to the tool holder. For example, if the sample handling apparatus can read out the identification code of the tool, it can be assumed that the tool is correctly coupled. If this does not succeed, the tool is probably not correctly coupled.

For the purpose of controlling and/or actuating the tool through the sample handling apparatus, the tool can also comprise, for example, a data processing device such as, for instance, a microprocessor, in which case the latter could communicate with an appropriate control device of the sample handling apparatus and could autonomously perform complex control of active and/or passive elements of the tool. For simplicity, however, the control of the tool is effected directly, through the activation or deactivation of appropriate active or passive elements such as, for instance, actuators, for example through simple switch-on or switch-off of the respective energy supply. Clearly, it is also possible in this case for the tool to comprise sensors or other structural elements that acquire data relating to the state of the tool or its interaction with other devices and that feed this data back to the sample handling apparatus, such that the control can be adapted if necessary.

However, it would also be possible for the tool itself to have a data processing device such as, for instance, a microprocessor, which communicates with the sample handling apparatus via the communication interface. In this case, clearly, a program for execution by the microprocessor could also be stored in the memory.

The memory can be both a volatile memory and a non-volatile memory. In addition, it can be a read-only memory, to which the data to be stored are written once and can then be read out again as often as required. Such read-only memories also exist as erasable and reprogrammable memories. Or it can be a re-writable memory, to which any data, for example a program or also configuration information, are written, and the stored information can be read out again as often as required. The sample handling apparatus could write into the memory, for example, the number of usages of the tool or, also, the operating period of the tool, such that it can be ascertained at any time, for example, whether the tool may continue to be used, whether a fault has occurred, whether servicing is required or whether the permitted number of usages has already been reached. On the basis of such information the sample handling tool could also initiate further processes such as, for example, providing the information to a user or starting a servicing or diagnostic process. Clearly, it is also possible for such information to be polled actively from the tool. Depending on the required behavior of the tool, for instance depending on the specific application, the sample handling apparatus could reprogram the memory and thus equip the tool with application-specific functions.

Upon, or following, the decoupling of the tool, the latter is typically deposited in a holder of the sample handling apparatus for keeping a decoupled tool, which holder is referred to in the following as a parking station, and the tool is held in interim storage until the next use. As soon as the tool is decoupled from the tool holder, the connections established upon coupling are disconnected, such that transmission of data or energy between the tool and the sample handling apparatus is no longer possible. Depending on the tool, this is also not a problem. However, there are tools for which a transfer of data and/or energy between the tool and the sample handling apparatus would be desirable, despite the tool not being coupled to the tool holder, for example if the sample manipulation device has to be preheated before use. The tool could then be correspondingly controlled in good time before it is coupled to the tool holder, such that the sample manipulation device is already preheated when the tool is coupled for use.

In the case of a preferred embodiment of the invention, the tool therefore comprises a corresponding communication interface for establishing a communication connection between the tool, which has been decoupled from the tool holder, and the parking station, i.e. between the tool and the sample handling apparatus.

Such a communication in the decoupled state could be achieved, for example, in that the tool would be provided with a radio interface, as already mentioned previously, such that an appropriate control device can communicate with the tool at any time via this radio interface, and control the tool.

However, in order that the tool does not have to be provided with its own energy supply, as likewise already mentioned, this communication interface also preferably comprises at least one, typically two or more, electrical contacts for the purpose of establishing at least one, or correspondingly more, electrically conductive connections between the tool and the parking station. Also in the case of this communication interface, the term communication is to be understood to include not only data transmission, but also energy transmission. Otherwise, for this communication interface for communication of the tool with the sample handling apparatus via a parking station, the same applies, as appropriate, as for the communication interface, described above, for communication via the tool holder.

In fact, even in the case of a communication interface for communication via a parking station, realized by means of direct electrical connections, the same communication connections could be used as for communication via the tool holder. However, since the realization of such a communication interface is more complex than a separate interface, the tool preferably comprises an additional communication interface, for example additional electrical contacts for establishing separate electrical connections to the parking station. These electrical connections are established automatically upon the tool being decoupled from the tool holder, i.e. upon the tool being deposited in the parking station, and are disconnected again upon the tool being coupled to the tool holder, i.e. upon the tool being taken up out of the parking station.

It is to be noted that the feature that is the communication interface is entirely independent of the features of the tool that are described in this document, being the tool holder or the sample handling apparatus. This also applies to all features connected with a communication interface as previously described, such as, for instance, a memory, a microprocessor, active or passive elements such as actuators or sensors that communicate via this interface or are controllable via same, a sample handling apparatus having a corresponding communication interface and/or a corresponding control device, a communication interface for communication with a parking station, etc.

Such a communication interface, and further features connected therewith, can therefore be integrated into a tool for a sample handling apparatus, a tool holder, a sample handling apparatus or also a parking station, this being, in particular, irrespective of whether the tool, the tool holder or the sample handling apparatus are or are not realized according to the invention. This means irrespective of whether the tool comprises a correspondingly realized holding device or the tool holder comprises corresponding fastening means, of the manner in which the tool is coupled to a sample handling apparatus or whether the tool or the tool holder is realized according to one of the preferred exemplary embodiments. It is also possible, for example, for a tool having such a communication interface (of whichever kind) to be able to be coupled to a sample handling apparatus despite the latter itself not even having a corresponding communication interface, thus for the tool either not to transmit any signals via this interface, or to communicate with another device via this interface, or to transmit energy via this interface.

In the case of certain tools it is necessary or at least useful if they comprise a connection for liquid and/or gaseous substances, for example, for the delivery and discharge of washing or rinsing liquids, or of substances with which the sample is to be made to react. Liquid or gaseous substances could also be used for the actuation of corresponding pneumatic or hydraulic elements of the tool.

Although such an interface is not necessary in the case of many tools, and could therefore also be omitted, the tool therefore, in the case of a further preferred embodiment, comprises at least one fluid interface for establishing at least one fluid connection between the tool and the sample handling apparatus, the term fluid being used, within the scope of this description, both for gaseous and for liquid substances.

The establishing and disconnecting of such a fluid connection is preferably effected simultaneously with, respectively, the coupling and decoupling of the tool to and from the tool holder. The fluid interface comprises, for example, a first element of a known plug-in coupling, the tool holder comprising a corresponding second element of such a plug-in coupling.

As already described, the tool holder of the sample handling apparatus is fastened to the sample handling apparatus, fastenable to the latter, or realized as part of the same, so as to be movable in a z direction. The tool holder, for example, is movably fastened to a tool receiver, which, in turn, is fastened to the slide of a sample handling apparatus. In the case of a sample handling apparatus that comprises a slide guide having a slide that is movable in one or in two differing, directions, which are usually perpendicular to one another, the tool receiver is typically fastened to an end of the slide. Accordingly, the tool holder is fastened to the sample handling apparatus so as to be movable perpendicularly, the perpendicular typically being designated as the z direction.

Preferably, therefore, the tool can also be coupled to and decoupled from the tool holder in the z direction.

The horizontal direction, or horizontal directions, in which the slide can be moved on the slide guide are typically designated as x, or x and y. However, this z direction need not necessarily be exactly perpendicular, but can also deviate slightly from the perpendicular, or the sample handling apparatus can be of an entirely different configuration, such that the z direction in which the tool holder can be moved can be any other spatial direction. Clearly, it is also possible for the tool holder, or the tool receiver, to be moved via one or more swivel arms, a combination of translational and rotational movements also being possible for the moving of the tool holder.

Typically, the tool receiver is fixedly fastened to the slide, for example screwed on, and preferably comprises a guide along which the tool holder can be moved. This guide can be realized, for example, as a groove or as a rail, the tool holder comprising the associated guided counterpart.

For the purpose of moving the tool holder on the sample handling apparatus in the z direction, the sample handling apparatus has a (first) drive, it being immaterial, in principle, precisely how this drive is designed. An appropriate drive can be selected according to the requirements for the speed and precision of the movements of the tool that are to be executed. Preferably, however, this drive comprises an electric motor, for example any direct-current motor or three-phase current motor or alternating-current motor, since an energy supply of electrical energy is typically already present. Advantageously, the electric motor is a stepping motor, which, in the case of appropriate control and corresponding design, can execute the required movements of the tool holder extremely rapidly and precisely. While the drive can also be realized as part of the movable tool holder and would be moved concomitantly, it is advantageous for this drive to be realized as part of the tool receiver (or of another element of the sample handling apparatus), since, for example, the mass to be moved can thereby be reduced.

A tool for handling a sample can now be coupled to, and obviously decoupled from, such a tool holder. For this purpose, the tool holder comprises first fastening means for detachably fastening a fastening device of the tool. According to the invention, the tool holder additionally comprises second fastening means, for detachably fastening a holding device of the tool, the first and second fastening means being movable relative to one another in the z direction. In this way, the holding device and the fastening device of a tool, which can be moved relative to one another in the coupling direction, can be simply coupled to the tool holder and, in the coupled state, moved relative to one another in the z direction. For coupling, the tool in this case is positioned, for example deposited in a parking station of the sample handling apparatus, in such a way that the coupling direction of the tool coincides with the z direction of the tool holder, thus, typically, perpendicularly, i.e. vertically or substantially vertically.

For the purpose of realizing the relative movement between the first and second fastening means in the z direction, the tool holder has a (second) drive, which again can be realized per se in any manner, according to the requirements of the respective application. In order to keep the number of components for the production of the sample handling apparatus as small as possible, the drive for moving the second fastening means on the tool holder is preferably the same as that for moving the tool holder on the tool receiver.

In the case of a preferred embodiment of a tool holder according to the invention, the first fastening means are fixedly fastened to the tool holder, and therefore cannot be moved in relation to the tool holder. On the other hand, the second fastening means are fastened to the tool holder so as to be movable in the z direction, the drive for moving these second fastening means in the z direction being realized such that the holding device of a tool, after being coupled to the tool holder, can be moved in the z direction by means of this second drive.

In order that a sample manipulation device of the tool can also be coupled to the tool holder, the latter, in the case of a further preferred embodiment variant, comprises third fastening means for detachably fastening a movable element of the sample manipulation device. Here, likewise, the first and third fastening means are movable relative to one another in the z direction, this being irrespective of a relative movement between the first and the second fastening means. This means that the second and third fastening means can be moved relative to one another in the z direction. In this way, a movable element can also be coupled to the tool holder in the z direction and, in the coupled state, moved in the coupling direction, i.e. in the z direction, in relation to the fastening device and independently of the holding device.

A drive is also required for the relative movement between the first and third fastening means, the same applying, as appropriate, to this drive as for the drive for moving the second or also the first fastening means.

In the case of a further preferred exemplary embodiment of the tool holder, again the first fastening means are fixedly fastened to the tool holder, and the third fastening means are fastened to the tool holder so as to be movable in the z direction by means of the drive, such that the movable element of the sample manipulation device can be moved in the z direction by means of this third drive after coupling. Accordingly, in the case of this example, on the one hand, the tool holder, together with the first fastening means, can be moved on the sample handling apparatus and, on the other hand, the second and third fastening means can be moved by means of the second and third drive, respectively, independently of one another and relative to one another, likewise in the z direction in each case.

A sample handling device according to the invention comprises a tool holder that is movable in the z direction, as just described, which is fastened or fastenable to the sample handling apparatus, for example a tool receiver, or is realized as part of the sample handling apparatus.

As already described above, the sample handling apparatus advantageously also comprises a communication interface for establishing a communication connection between the sample handling apparatus and the tool. This communication interface is preferably realized in the form of electrical contacts that are realized, for example, as part of the tool holder, such that, upon coupling of a tool having corresponding electrical contacts, one or more electrical connections are established automatically between the sample handling apparatus and the tool. As likewise already described, these electrical connections can be used both for the transmission of data and for the transmission of energy. For the purpose of generating or processing signals that are to be transmitted via this communication interface, the sample handling apparatus typically comprises one or more corresponding signal sources such as, for example, a data processing device or an electric power supply—or is connected to such—the communication interface being connected to this signal source or these signal sources.

For the purpose of exchanging information with the tool, for example the processing of tool-specific data received from the tool via the communication interface, or for the transmission of control signals to the tool, the sample handling apparatus preferably comprises a microprocessor, as well as suitable transmitters and receivers for transmission of the signals.

For the purpose of supplying energy to the sample handling apparatus and to the tools coupled thereto, the sample handling apparatus is preferably connected to a standard electric power supply network.

In another preferred embodiment, the sample handling apparatus also comprises a fluid interface, such that it is also possible to connect tools for which the delivery or discharge of a fluid during operation is necessary or useful.

A sample handling arrangement according to the invention comprises a sample handling apparatus having a tool holder as just described and at least one, but typically two or more, tools according to the invention, one of these tools in each case being fastenable to the sample handling apparatus.

For the purpose of storing these tools, the sample handling arrangement advantageously has a parking station, as likewise already described above.

The method according to the invention for coupling and decoupling a tool according to the invention to and from, respectively, a tool holder of a sample handling apparatus is distinguished in that, firstly, the tool holder and the tool are positioned in a mutually appropriate manner. The tool is then coupled to or decoupled from the tool holder exclusively through relative movements of the tool holder, the second fastening means, the fastening device and/or the holding device. This coupling or decoupling in this case is effected in the z direction, which, as already described, corresponds to the coupling direction in which the holding device can be moved relative to the fastening direction, as described.

This means that, for the purpose of coupling the tool, the tool holder is positioned in such a way that fastening means (of the tool holder) and connecting elements (of the tool, which, typically, is deposited in a parking station) that correspond to one another lie, as it were, over one another in the z direction.

The tool can then be coupled to the tool holder through a single active movement of the tool holder in the z direction towards the tool and a single active movement of the tool holder in the z direction away from the tool. Only the locking of the connecting devices necessitates, at most, a brief interruption or a slowing of such an active movement in the z direction, or an additional active movement of the individual element in the z direction is required. This means that the raising of the tool following coupling is also effected in the z direction, this raising movement also being able to be used simultaneously for locking the connections. This means that both the moving of the tool holder towards the tool, the coupling and the raising of the tool are effected in the same direction, namely, the z direction. The same also applies in the case of decoupling, in which a movement of individual elements in the z direction can be used to unlock the connecting devices.

If the tool to be coupled also comprises a sample manipulation device having a movable element that is to be coupled, this is preferably coupled to or decoupled from the tool holder substantially simultaneously with the coupling or decoupling of the holding device and of the fastening device, likewise through mutual relative movements.

Further advantageous embodiments and feature combinations of the invention are disclosed by the following detailed description and the claims in their totality.

BRIEF DESCRIPTION OF THE DRAWINGS

The drawings used to explain the exemplary embodiment show:

FIG. 1 a schematic representation of a sample handling apparatus according to the invention;

FIG. 2 a schematic representation of a tool receiver, comprising a tool holder according to the invention fastened thereto;

FIG. 3 a schematic representation of a tool according to the invention;

FIG. 4 a schematic detailed view of a holding device of the tool from FIG. 3;

FIG. 5 a schematic representation of the tool from FIG. 3, coupled to the tool holder from FIG. 2;

FIG. 8 a detailed, oblique top view of a tool according to the invention;

FIG. 9 a detailed, oblique bottom view of the tool from FIG. 8;

FIG. 10 a schematic representation of a parking station;

In principle, in the figures, corresponding parts are denoted by corresponding references.

METHODS FOR IMPLEMENTATION OF THE INVENTION

Figures 6, 7:
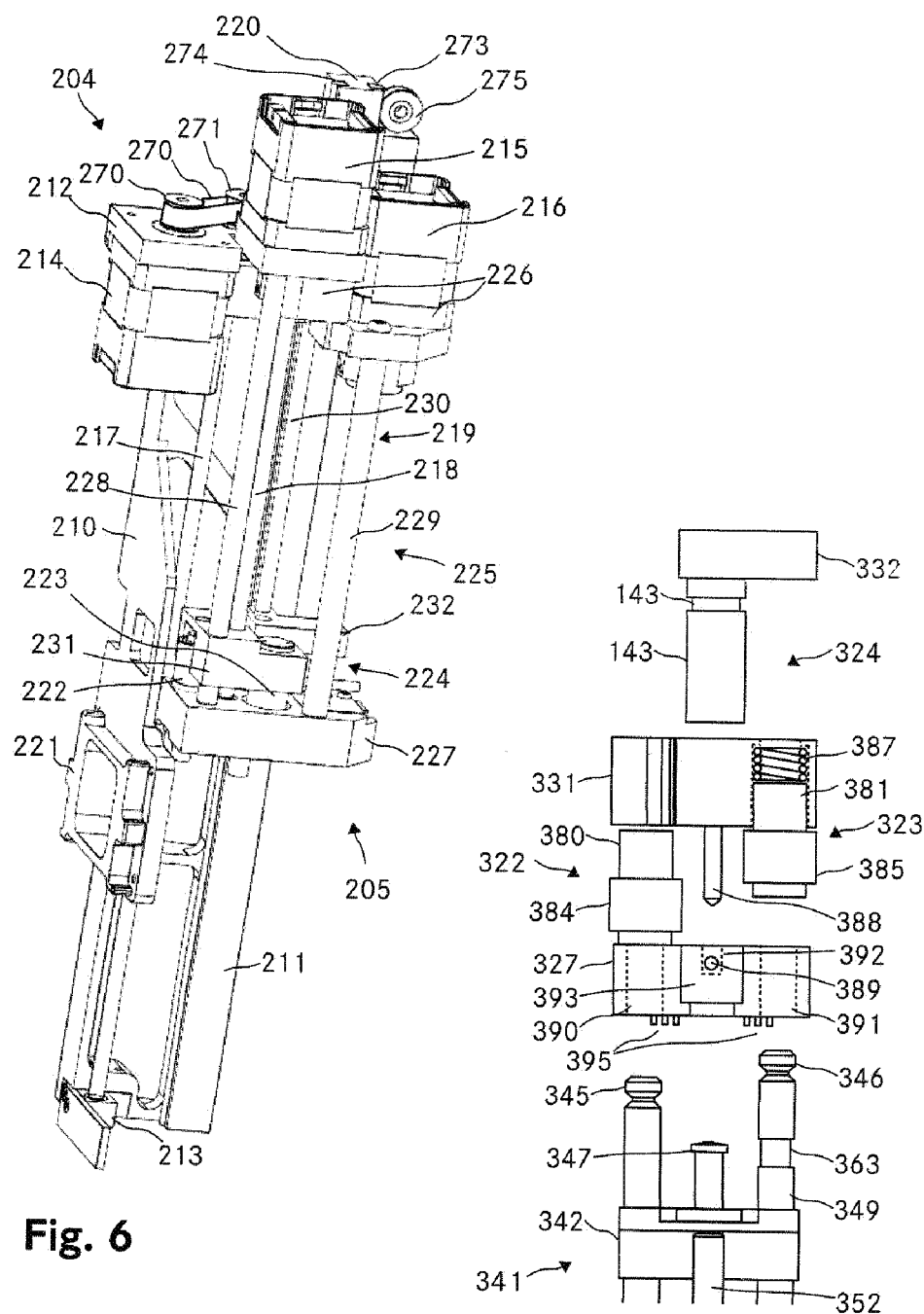
FIG. 6 a more detailed representation of a further tool receiver according to the invention, with tool holder fastened thereto.
FIG. 7 a schematic representation of the coupling mechanism between a tool and a tool holder, before coupling.

FIG. 1 shows a schematic, perspective representation of a sample handling apparatus, realized as an autosampler 1. The autosampler 1 comprises a slide guide 2, a transverse slide 3 that is movably fastened to the slide guide 2, and a tool receiver 4, which is fastened to the transverse slide 3 and to which, again, a tool holder 5 is movably fastened. The slide guide 2 is elongate in form and defines a horizontal x direction 6, in which the transverse slide 3, likewise elongate in form, can be moved along the slide guide 2. In addition, the transverse slide 3 can be moved on the slide guide 2 in a y direction 7, which is horizontal and perpendicular to the x direction 6. By means of corresponding drives, therefore, the transverse slide 3 can be moved in a discretionary manner in a horizontal plane on the slide guide 2.

The tool holder 5 is again fastened to the tool receiver 4 so as to be perpendicularly movable by means of a corresponding drive, and thus defines a z direction 8, which is at right angles to the horizontal plane defined by the x direction 6 and the y direction 7.

The tool holder 5 can therefore be moved in the x direction 6, the y direction 7 and the z direction 8, independently from one another in each case, such that, through appropriate control of the drives, it can be positioned at practically any optional point of the three-dimensional space within the range of the tool holder 5 in front of the slide guide 2.

Further, the autosampler 1 comprises a tool storage means 9, which is fastened to the slide guide 2 and in which a plurality of tools that can be coupled to the tool receiver 4 can be kept, and the autosampler stands on feet 10.

FIG. 2 shows a schematic representation of a tool receiver 104, comprising a tool holder 105 fastened thereto so as to be vertically movable (according to representation), and FIG. 3 shows a tool 140 that can be coupled to this tool holder 105.

For the purpose of fastening to the tool holder 105, the tool 140 comprises a fastening device 141, having an adapter plate 142 and a holder plate 143, which are rigidly connected to one another through a base 144. Fixedly connected to the adapter plate 142 is a fastening element, here in the form of a male coupling element 145 of a plug-in coupling.

Fastened to the tool 140 is a sample manipulation device having a movable element, here in the form of a syringe 150 having a cylindrical syringe body 151, a piston that is movable at the lower end of a piston rod 152 and in the syringe body 151, and a hollow needle 153, fastened to the lower end of the syringe body 151. Fastened to the upper end of the piston rod 152 is a fastening element, again in the form of a male coupling element 147 of a plug-in coupling, the piston being movable in the syringe body 151, in the direction of the arrow 155, by means of the piston rod 152.

The tool 140 further comprises a holding device 160, comprising a bar 161 that is held so as to be movable in corresponding recesses of the adapter plate 142 and the holder plate 143. Fastened to the lower end of the bar 161 is a needle guide 163, which has a hole 164, through which the hollow needle 153 of the syringe 150 fits precisely. FIG. 4 shows a top view of the holding device 160. At the upper end of the bar 161 there is a further fastening element, again in the form of a male coupling element 146 of a plug-in coupling, the holding device 160 being movable, together with the needle guide 163, in the direction of the arrow 165.

If, for example, the holding device 160 is then spatially fixed and the fastening device 141 is moved in the direction indicated by the arrow 165, the hollow needle 153 moves, accordingly, up or down in the hole 164 and is thus guided by the needle guide 163.

The tool receiver 104 comprises a rigid frame, comprising a back wall 110, a side wall 111, a top plate 112 and a bearing plate 113. Realized on the side of the back wall 110 that faces away from the tool holder 105 is a coupling plate 121, by means of which the tool receiver 104 can be fixedly fastened, for example screwed on, to a transverse slide 3 of a sample handling apparatus 1.

A guide 120 serves to guide the tool holder 105 in the vertical direction, the guide 120 being able to be clamped between the top plate 112 and the bearing plate 113 or, as in the present example, realized on the inside of the side wall 111. Further, fastened to the top plate 112 is a motor 114, to the rotary axle of which there is flange-connected a shaft 117, which is provided with an external thread and which is guided through a corresponding recess in the top plate 112 to the bearing plate 113, in which the shaft 117 is rotatably mounted.

The tool holder 105 comprises a frame 125, which is guided by the guide 120, and which comprises a top plate 126 and a bottom plate 127 that are rigidly connected to one another by stay bars 128, 129. The frame 125 comprises guided elements that match the guide 120, such as, for example, corresponding recesses in the top plate 126 and in the bottom plate 127. The shaft 117 also is guided by one or more corresponding recesses in the top plate 126 and in the bottom plate 127, one of these recesses typically having an internal thread that matches the external thread of the shaft 117 and meshes therein. If the shaft 117 is then made to rotate by the motor 114, the frame 125 is moved upwards or downwards, depending on the direction of rotation.

Further, a connecting element is fastened to the bottom plate 127. This connecting element is realized here as a female coupling element 122 of a plug-in coupling, and serves to couple the fastening device 141 of the tool 140 or, more precisely, to couple the matching male coupling element 145. Since the tool 140 (according to representation) is coupled to the tool holder 105 from below, the female coupling element 122 could also be mounted on the underside of the bottom plate 127. In this example, however, it is mounted on the upper side of the bottom plate 127, directly over a corresponding recess, through which the male coupling element 145 of the tool 140 can be guided.

The guide 120 in this case both guides the frame 125 in the vertical direction and nevertheless also, at the same time, prevents the frame 125 from rotating about the vertical axis defined by the shaft 117. The guide 120 could also be omitted, in which case the shaft 117 serves not only to move the tool holder 105 vertically, but also to guide it in the vertical direction. Accordingly, it would be necessary to ensure by other means that the frame 125 does not rotate about the shaft 117.

Fastened to the top plate 126 are two further motors 115, 116, to the rotary axles of which there is flange-connected, respectively, a shaft 118, 119 provided with an external thread. Both shafts 118, 119 are rotatably mounted in corresponding recesses of the top plate 126 and of the bottom plate 127, such that they can be made to rotate counter-clockwise or clockwise by the respectively associated motor 115, 116.

For the purpose of coupling the holding device 160 of the tool 140, the tool holder 105 further comprises a second female coupling element 123 of a further plug-in coupling, which coupling element is fastened to a coupling plate 131 in such a way that the counterpart of the plug-in coupling that is present on the holding device of the tool 140, being the male coupling element 146, can again be inserted from below into the female coupling element 123. For this purpose, there are also corresponding recesses in the bottom plate 127. The coupling plate 131 itself again comprises a recess, which is provided with an internal thread and through which the shaft 118 is guided, such that the coupling plate 131 can be moved upwards or downwards, together with the female coupling element 123, by a rotation of the shaft 118. Again, the shaft 118 itself can serve to vertically guide the coupling plate 131, or a separate guide is provided. In this example, the stay bar 128 serves to guide the coupling plate 131.

Accordingly, the tool holder 105, for the purpose of coupling a further movable element of the tool 140 that is present in any case, being here the piston rod 152 with the piston fastened thereto, comprises a third female coupling element 124 of a third plug-in coupling. This coupling element 124 is again fastened to a further coupling plate 132 in such a way that the coupling element 147 of the piston rod 152 can again be inserted from below into the female coupling element 124. For this coupling element 147 of the tool 140, also, the bottom plate 127 has corresponding recesses. The coupling plate 132 itself likewise again comprises a recess, which is provided with an internal thread and through which the shaft 119 is guided, such that the coupling plate 132 can be moved upwards or downwards, together with the female coupling element 124, by a rotation of the shaft 119. Again, the shaft 119 itself can serve to vertically guide the coupling plate 132, or a separate guide is provided. In this example, the stay bar 129 serves to guide the coupling plate 132.

In this example, the motors 114, 115, 116 are realized as stepping motors.

FIG. 5 shows a schematic representation of the tool from FIG. 3, coupled to the tool holder from FIG. 2. In this case, the male coupling elements 145, 146, 147 are each guided from below through corresponding recesses in the bottom plate 127 of the frame 125 and coupled to the respectively corresponding female coupling elements 122, 123, 124.

In this way, on the one hand, the tool holder 105, together with the fastening device 141 coupled thereto, can be moved vertically relative to the tool receiver 104 by means of the motor 113. And, on the other hand, the holding device 160 and the piston rod 152, together with the piston, can be moved, independently of one another, vertically in relation to the fastening device 141 by means of the motors 114, 115, the hollow needle 153 being guided by the needle guide 163.

In FIG. 5, as compared with FIG. 3, the holding device 160 is represented as having been displaced upwards in relation to the fastening device 141, and the piston rod 152, together with the piston, is represented as having been displaced downwards in the syringe body 151.

FIG. 6 shows a more detailed representation of a further tool receiver 204 according to the invention, with a tool holder 205 fastened thereto.

The tool receiver 204 comprises a rigid frame, comprising a back wall 210, a side wall 211, a top plate 212 and a bearing element 213 that is fastened to the back wall 210 and to the side wall 211, a coupling plate 221, for fastening to a transverse slide, again being provided on the back side of the back wall 210. These elements, referred to as walls, are not realized so as to be continuous, but have various recesses.

Further, fastened to the underside of the top plate 212 on the outside of the back wall 210 of the tool receiver 204 is a motor 214, the rotary axle of which projects upwards through an opening in the top plate 212 and to which there is fastened a drive wheel 270, which, via a belt 272, drives a further drive wheel 271 that is fastened to a shaft 217 provided with an external thread. The shaft 217 is again guided through a corresponding recess in the top plate 212 to the bearing element 213 and is thereby rotatably mounted, and can be made to rotate by the motor 214. The shaft 217 is provided with an external thread, and the guide 220 for guiding the tool holder 205 is a rail, having lateral guide bars 273, 274, which is realized vertically on the inside of the side wall 211.

The tool holder 205 comprises a frame 225, which comprises a top plate 226 and a bottom plate 227 that are rigidly connected to one another by stay bars 228, 229, 230. The shaft 217 passes through an opening in the top plate 226, which is provided with an internal thread matching the external thread of the shaft 217, such that the frame 225 can be moved upwards or downwards by rotation of the shaft 217. Additionally, a plurality of guide rollers 275 are fastened to the top plate 226, some of these guide rollers 275 running along the guide bars 273, 274 on one side of the rail and others of the guide rollers 275 doing so on the other side of the rail.

Further, fastened to the bottom plate 227 is a female coupling element 222 of a plug-in coupling, which element serves to couple the fastening device of a tool.

Fastened to the top plate 226 are two further motors 215, 216, to the rotary axles of which there is flange-connected, respectively, a shaft 218, 219 provided with an external thread (shaft 219 is not visible in FIG. 6). Both shafts 218, 219 are rotatably mounted in corresponding recesses of the top plate 226 and of the bottom plate 227, such that they can be made to rotate counter-clockwise or clockwise by the respectively associated motor 215, 216.

The tool holder 205 further comprises a second female coupling element 223 of a further plug-in coupling, which coupling element is fastened to the underside of a coupling plate 231, such that the holding device of a tool can be coupled thereto. The coupling plate 231 again comprises a recess, which is provided with an internal thread and through which the shaft 218 is guided, such that the coupling plate 231 can be moved upwards or downwards, together with the female coupling element 223, by a rotation of the shaft 218. The stay bar 228 is guided through a corresponding opening of the coupling plate 231, for the purpose of vertically guiding the coupling plate 231.

Accordingly, for the purpose of coupling a syringe piston of a syringe, the tool holder 205 comprises a third female coupling element 224 (not visible) of a third plug-in coupling. This coupling element 224 is again fastened to the underside of a further coupling plate 232. The coupling plate 232 likewise comprises a recess, which is provided with an internal thread and through which the shaft 219 is guided, such that the coupling plate 232 can be moved upwards or downwards, together with the female coupling element 224, by a rotation of the shaft 219. The stay bar 229 again serves to vertically guide the coupling plate 232.

In this example, the motors 214, 215, 216 are realized as stepping motors.

FIG. 7 shows the coupling mechanism between a tool and a tool holder. Represented is a bottom plate 327 of a tool holder together with a female coupling element 322 fastened thereto, a coupling plate 331 of the tool holder together with a female coupling element 323 fastened thereunder and therein, and the adapter plate 342 of a fastening device 341 of a tool to be coupled, together with a male coupling element 345 fixedly fastened thereon, a needle guide 363 that is fastened to the adapter plate 342 so as to be movable in the vertical direction in a guide sleeve 349 and at the upper end of which there is a male coupling element 346, and a piston rod 352, at the upper end of which there is a further male coupling element 347. A further coupling plate 332, together with a female coupling element 324, is shown above the coupling plate 331.

The two coupling elements 322, 323 each comprise a cylindrical coupling body 380, 381 of circular cross-section having a spring-loaded ring 384, 385 that is displaceable on its surface. Owing to the spring, the ring 384, 385 is in each case held in the position, represented in FIG. 7, at the lower end of the coupling body 380, 381, and thus locks the coupling. If the ring 384, 385 is pushed upwards, contrary to the spring force, the coupling becomes unlocked and the corresponding, matching male coupling elements can be introduced without resistance into the female coupling elements 322, 323.

Coupling of the fastening device 341 and of the needle guide 363 of the tool is effected as follows: Firstly, the bottom plate 327 and the coupling plate 331 are brought together, the coupling body 380 being moved into a recess of the coupling plate 331, but the ring 384 being pressed downwards by the coupling plate 331 and thus unlocking the coupling element 322. At the same time, the coupling body 381 is moved into a recess of the bottom plate 327, the ring 384 here being pressed upwards by the bottom plate 327 and thus unlocking the coupling element 323. In addition, a pin 388, which is fastened on the underside of the coupling plate 331, is introduced into an opening 392 of the bottom plate 327. Projecting into this opening 392 is a further pin 389, which is mounted horizontally and with spring loading in the bottom plate 327, and which is displaced horizontally, contrary to the force of the spring, by the pin 388, such that it projects slightly into an upwardly directed opening 393.

The adapter plate 342 is then moved on to the bottom plate 327 from below, such that the male coupling elements 345, 346 of the tool are introduced into the female coupling elements 322, 323 through corresponding openings 390, 391 in the bottom plate 327. At the same time, the coupling element 347 is introduced into the opening 393 from below.

Finally, the coupling plate 331 is raised slightly, such that the ring 384 locks the coupling element 322. In order that the coupling body 381 of the coupling element 323 is not thereby raised from the coupling element 346, the coupling body 381 is supported in the coupling plate 331 by a spring 387, which presses the coupling body 381 downwards, contrary to the movement of the coupling plate 331, and thus ensures that only the non-spring-loaded ring 385 moves upwards and thus locks the coupling element 323. The spring 387, for example in the case of a spring travel of approximately 3 mm, has a spring force of approximately 8 newtons. This means that, for the purpose of locking the coupling element 322, the coupling plate 331 is raised by approximately 3 mm.

Coupling of the piston rod 352 is effected substantially simultaneously, in that the coupling plate 332 is moved downwards. In this case, the coupling element 324 is introduced into the opening 393 of the bottom plate 327 and, by means of the pin 389, the ring 386 is pushed upwards on the coupling body 382, such that the coupling element 324 becomes unlocked. The corresponding male coupling element 347 is actually already present in this opening 393. Upon the coupling plates 331, 332 being raised, the pin 388 then releases the pin 389, as a result of which the coupling element 324 becomes locked.

In this way, the fastening device 341, the needle guide 363 and the piston rod 352, together with the piston of a syringe, are coupled simultaneously to the tool holder 305 through exclusively vertical movements, i.e. the direction previously referred to as the coupling direction or, also, z direction.

Whether the tool is correctly coupled can be determined, as already mentioned previously, from whether particular data can be transmitted and received via the electrical connections established during coupling. In addition, the tool holder, or the tool, can comprise a further device, by means of which it can be verified whether the movable element of the tool, thus in this case, for example, the piston rod 352, has also been correctly coupled to the bottom plate 327. This could be effected, for example, in that a magnet is appropriately mounted on one of these two elements and a Hall sensor is appropriately mounted on the respective other element. For example, the movable element comprises a magnet, such that a Hall sensor mounted on the tool holder supplies a particular signal only if the movable element has been correctly coupled, i.e. the magnet is in the intended position. Correct coupling could also be effected in that the coupled tool is guided past a light barrier in such a way that the light beam is interrupted, or remains uninterrupted, depending on requirement, only if the movable element is correctly coupled. Clearly, this coupling detection can be effected in other ways, for example by means of appropriate capacitive, inductive or, also, purely mechanical switches or other elements.

Decoupling is effected in that the bottom plate 327 and the coupling plate 331 are brought together, such that all three coupling elements 322, 323 and 324 become unlocked simultaneously, and the adapter plate 342 is then moved away downwards.

In addition, a plurality of contact pins 395 are represented on the underside of the bottom plate 342. These contact pins are spring-mounted in the bottom plate 327 and, upon coupling of the adapter plate 342, each establish an electrical contact to respectively one corresponding electrical contact surface (not visible) on the top side of the adapter plate 342. The contact pins 395 are electrically connected to a data processing device (not represented) of the sample handling apparatus. These electrical connections serve, for example, to control or actuate grippers, valves, heaters or other manipulators of the tool or, also, to feed back sensor data, for example from temperature sensors of the tool.

FIGS. 8 and 9 each show an oblique view of a tool 440 according to the invention, once obliquely from above with a syringe 450 inserted therein, and once obliquely from below without a syringe. The tool 440 comprises a fastening device 441, having an adapter plate 442 and a holder plate 443, which are rigidly connected to one another through a base, here in the form of two guide sleeves 449. On the top side of the adapter plate 442 there is a male coupling element 445, as well as a plurality of electrical contact surfaces 496 for establishing electrical connections between the tool holder and the tool.

The syringe 450 is introduced into corresponding openings of the adapter plate 442 and of the holder plate 443, and fastened to the adapter plate 442 by means of a flange 454. It comprises a piston rod 452 having a male coupling element 447 realized at its upper end.

The tool further comprises a holding device 460, which comprises two bars 461, which are movably guided in the guide sleeves 449, and fastened to the lower end of which there is a needle guide 463. The needle guide 463 comprises a replaceable guide element 466, the hole 464 of which can be matched to the diameter of the hollow needle 453 of the syringe 450. A male coupling element 446 is fastened to the upper end of one of the bars 461 for the purpose of coupling the holding device 460 to a tool holder.

A magnet, which, as already mentioned, can be used for opening sample containers, can be provided on the back side of the needle guide 463, on the holder represented in FIGS. 8 and 9.

The previously mentioned magnets (not represented) for transporting sample phials could be mounted, for example, on the underside of the guide element 466.

The hollow needle 453 of the syringe 450 is guided, on the one hand, through the hole 464 in the guide element 466 of the needle guide 463 and, on the other hand, through the hole 468 in an antikink device 467, which is fastened on the underside of the holder plate 443.

Fastened on the underside of the adapter plate 442 is a printed circuit board 497, which is electrically connected to the contact surfaces 496 and which comprises a memory for storing any data, for example an erasable, programmable read-only memory such as, for instance, an EPROM or an EEPROM. The printed circuit board 497, on its underside, comprises further electrical contact surfaces 498, which serve to establish electrical contacts between the printed circuit board 497 and corresponding contact pins 495 of a parking station 499, in which the tool 440 can be placed for storage.

Such a parking station 499 is represented schematically in FIG. 10. For the purpose of mechanical coupling between the tool 440 and the parking station 499, the underside of the adapter plate 442 is provided with a pin 488, which is introduced into a corresponding opening 490 when the tool is being parked in the parking station 499.

Figure 11:
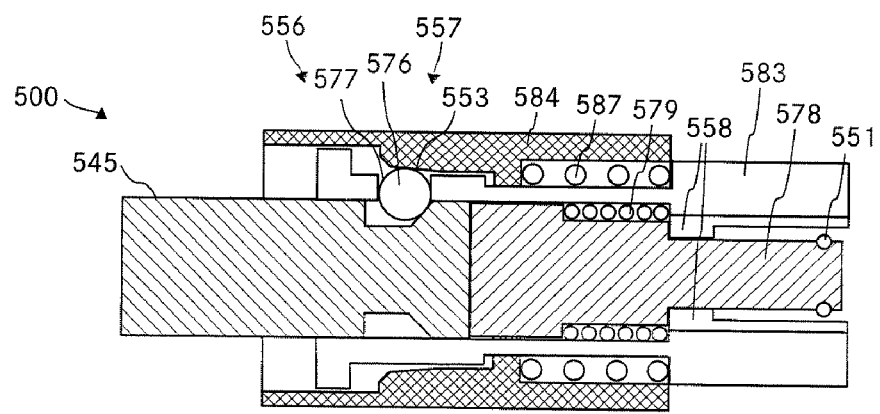
FIG. 11 a schematic detailed view of an unlocked plug-in coupling.
Figure 12:
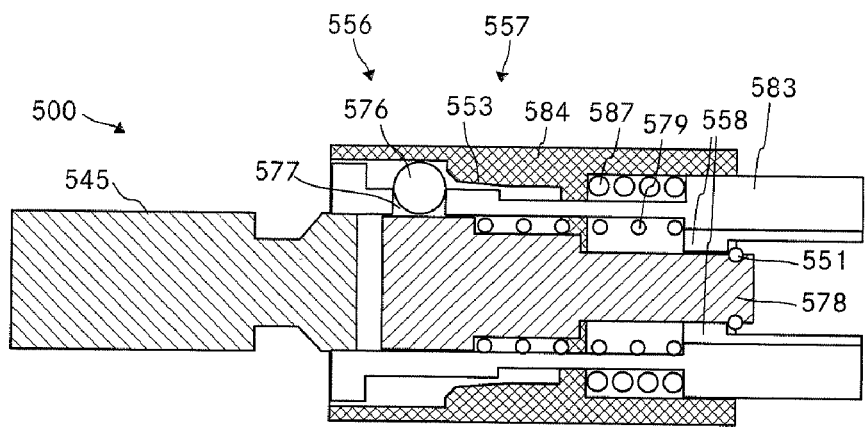
FIG. 12 a schematic detailed view of the plug-in coupling from FIG. 11, in the locked state.

FIGS. 11 and 12 each show a schematic detailed view of a plug-in coupling 500 without play, such as that used, for example, for coupling the fastening device and the syringe piston of a tool to the tool holder of an autosampler. FIG. 11 shows the plug-in coupling 500 in the coupled state, and FIG. 12 shows the plug-in coupling 500 before the male coupling element 545 has been coupled to the female coupling element 522.

The female coupling element 522 comprises a coupling body 580 having a sleeve 583, a ring 584 that is displaceable on the sleeve 583 and contrary to the force of a spring 587 supported on the sleeve 583, and an unlocking element 578 that is displaceable in the sleeve 583 and contrary to the force of a further spring 579 supported on the sleeve 583. The ring 584 has a large inner diameter in the end region 556 that faces towards the male coupling element 545. Adjoining this region is a clamping region 557 of the ring, which has a decreasing inner diameter, owing to a tapering bevel 553.

The sleeve 583 has a recess 577, in which a ball 576 is radially displaceable in relation to the longitudinal axis of the plug-in coupling 500. The male coupling element 545 comprises a coupling head 568, which is fastened to a piston rod 552 and separated by a continuous groove 569.

In the coupled state, the groove 569 is located in the region of the recess 577, such that the ball 576 is pressed, through the recess 577, into the groove 569 by the bevel 553 of the sleeve 583, which is pressed to the left (according to representation) by the force of the spring 587. The ball 576 thereby exerts a force directed towards the right upon the bevel 554 on the back side of the coupling head 568, and thereby also upon the unlocking element 578 with which the coupling head 568 is in contact. The action of this force causes the unlocking element 578 to be pressed, contrary to the force of the spring 579, onto the stop 558 provided on the inside of the sleeve 583.

The force exerted upon the coupling head 568 by the ball 576, and the counter-force exerted on the unlocking element 578 by the stop 558 then ensure that the plug-in coupling is without play. Critical for this is the angle of the bevel 553 in relation to the longitudinal axis of the plug-in coupling 500. This angle is preferably an angle in the range of between 2 and 15 degrees. If the angle is too great, the clamping effect becomes too small; if the angle is too small, the ball 576 can no longer be pushed sufficiently into the recess 577. Particularly preferred, therefore, is an angular range of between 2 and 5 degrees, since in this range a particularly good compromise between these two requirements can be achieved.

For the purpose of unlocking the plug-in coupling 500, it is necessary only for the ring 584 to be displaced contrary to the force of the spring 587 on the sleeve 583, such that the end region 556 is located in the region of the ball 576. Owing to the force of the spring 579, the unlocking element 578 is then pressed to the left, such that the ball 576 is pressed radially outwards, through the recess 577, by the bevel 554, and the plug-in coupling 500 thus becomes unlocked. The male coupling element 545 can then be removed, or is ejected from the sleeve 583 by the unlocking element 578. In order that the unlocking element 578 is not likewise ejected from the sleeve 583, it comprises, at its other end, a stop 551 in the form of a full-perimeter ring.

In summary, it may be stated that the invention makes it possible to create a sample handling apparatus and associated tools of such design that they can be exchanged extremely easily and automatically, and are nevertheless robust, such that they can be applied in an extremely flexible and variable manner.

The invention claimed is:

1. Tool for handling a sample, comprising a fastening device for detachably fastening the tool to a tool holder of a sample handling apparatus, and comprising a sample manipulation device fastened to the fastening device, characterized in that the tool comprises a holding device, which
   a) is fastened to the fastening device so as to be movable in a coupling direction and
   b) can be coupled to and decoupled from the tool holder in the coupling direction;
   c) the holding device comprises a first connecting element of a second positive-fit connecting device and the tool holder comprises a second connecting element of the second positive-fit connecting device,
   d) the holding device can be coupled to and decoupled from the tool holder through connecting and undoing, respectively, of the second positive-fit connecting device; and
   e) the fastening device being able to be coupled to and decoupled from the tool holder in the coupling direction,
   f) the fastening device comprising a first connecting element of a first positive-fit connecting device,
   g) the tool holder comprising a second connecting element of the first positive-fit connecting device, and
   h) the fastening device being able to be coupled to and decoupled from the tool holder in the coupling direction through connecting and undoing, respectively, of the first positive-fit connecting device.

2. Tool according to claim 1, the holding device comprising a guide element for guiding an element of the sample manipulation device that is in the form of a hollow needle, a longitudinal axis of the element in the form of a hollow needle being aligned in the coupling direction, and the guide element having an opening that is complete all the way round for guiding the element in the form of a hollow needle.

3. Tool according to claim 1, the first connecting device being realized without play.

4. Tool according to claim 1, the holding device being able to be coupled to and decoupled from the tool holder through connecting and undoing, respectively, of the second positive-fit connecting device in the coupling direction.

5. Tool according to claim 1, the tool comprising an element that is movable in the coupling direction, the movable element comprising a first connecting element and the tool holder comprising a second connecting element of a third positive-fit connecting device, the moveable element being able to be coupled to and decoupled from the tool holder in the coupling direction.

6. Tool according to claim 5, the sample manipulation device comprising a syringe that has a cylindrical hollow body fastened to the fastening device and has a piston that is movable in the hollow body and constitutes the movable element, and comprising a cannula that is fastened to the syringe and constitutes an element in the form of a hollow needle.

7. Tool according to claim 1, the tool comprising a communication interface for establishing a communication connection between the tool and the sample handling apparatus.

8. Tool according to claim 7, the tool comprising a memory in which there can be stored tool-specific data that can be transmitted directly to the sample handling apparatus via the communication interface.

9. Tool according to claim 7, having an additional interface for establishing at least one communication connection between the tool and a parking station of the sample handling apparatus that is realized for storing a decoupled tool.

10. Tool according to claim 1, having a fluid interface for establishing at least one fluid connection between the tool and the sample handling apparatus.

11. Tool according to claim 1, wherein the tool holder has a drive.

12. Tool according to claim 5, wherein the third connecting device being realized without play.

13. Tool according to claim 7, wherein the communication connection comprises at least one electrical contact for the purpose of establishing at least one electrically connective connection between the tool and the sample handling apparatus.

14. Tool according to claim 11, wherein the drive is an electric motor.

15. Tool according to claim 14, wherein the electric motor is a stepping motor.

* * * * *